(12) United States Patent
Bach et al.

(10) Patent No.: US 6,713,053 B1
(45) Date of Patent: Mar. 30, 2004

(54) USE OF IL-7 FOR TREATING AUTO-IMMUNE DISEASES AND INSULIN-DEPENDENT DIABETES MELLITUS IN PARTICULAR

(75) Inventors: Jean Francois Bach, Paris (FR); Jean Marc Gombert, Poitiers (FR); Andre Herbelin, Malakoff (FR); Michel Morre, Boulogne (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/125,168

(22) PCT Filed: Feb. 26, 1997

(86) PCT No.: PCT/FR97/00343

§ 371 (c)(1),
(2), (4) Date: Aug. 18, 1998

(87) PCT Pub. No.: WO97/31648

PCT Pub. Date: Sep. 4, 1997

(30) Foreign Application Priority Data

Feb. 28, 1996 (FR) .............................................. 96 02501

(51) Int. Cl.$^7$ ........................ A61K 45/00; A61K 35/14; A61K 38/00
(52) U.S. Cl. .......................... 424/85.2; 424/534; 514/2; 514/12
(58) Field of Search ................ 424/85.2, 534; 514/2, 12

(56) References Cited

U.S. PATENT DOCUMENTS 5,032,396 A * 7/1991 Williams et al. ............ 424/85.2

FOREIGN PATENT DOCUMENTS

| WO | WO 92/01459 | 2/1993 |
|---|---|---|
| WO | WO 96/01122 | 1/1996 |

OTHER PUBLICATIONS

Morrow WJ et al. AIDS virus infection and autoimmunity: a perspective of the clinical, immunological, and molecular origins of the autoallergic pathologies associated with HIV disease. Clin Immunol Immunopathol. Feb. 1991;58(2):163–80.*
Bach et al. The NOD mouse. Res. Immunol. 1997. vol. 148, pp. 285–366.*
Schnittman SM, Fauci AS. Human immunodeficiency virus and acquired immunodeficiency syndrome: an update. Adv Intern Med. 1994;39:305–55.*
Carini C, Essex M. Interleukin 2–independent interleukin 7 activity enhances cytotoxic immune response of HIV–1–infected individuals. AIDS Res Hum Retroviruses. Feb. 1994;10(2):121–30.*
FASEB Journal, vol. 4, No. 7, p A2183, 1990.
Database MEDLINE, Costello et al., Europena Journal of Medicine, May 1992, 1 (2) 119–21.
Immunology, vol. 80, No. 3, pp. 451–457, Nov. 1, 1993.
J. Immunology, vol. 155, pp. 4544–4550, 1995.
J. Exp. Med. vol. 178, pp. 87–99, Jul. 1993.
J. Exp. Med. vol. 178, pp. 901–908, 1993.
J. Exp. Med. vol. 180, pp. 653–661, 1994.
Autoimmunity, vol. 15, pp. 113–122, 1993.
C.R. Acad. Sci. Paris, Sciences de la vie/Life Sciences, vol. 319, pp. 125–129, 1996.

* cited by examiner

*Primary Examiner*—Yvonne Eyler
*Assistant Examiner*—Joseph F. Murphy
(74) *Attorney, Agent, or Firm*—Paul E. Dupont; Michael D. Alexander

(57) ABSTRACT

The use of interleukin 7 or T cells pre-incubated in the presence of IL-7 for preparing a drug or pharmaceutical composition for treating an auto-immune disease, particularly an auto-immune disease induced by a defect in CD4+ T cell immunoregulation, is disclosed.

1 Claim, 2 Drawing Sheets

Figure 1:
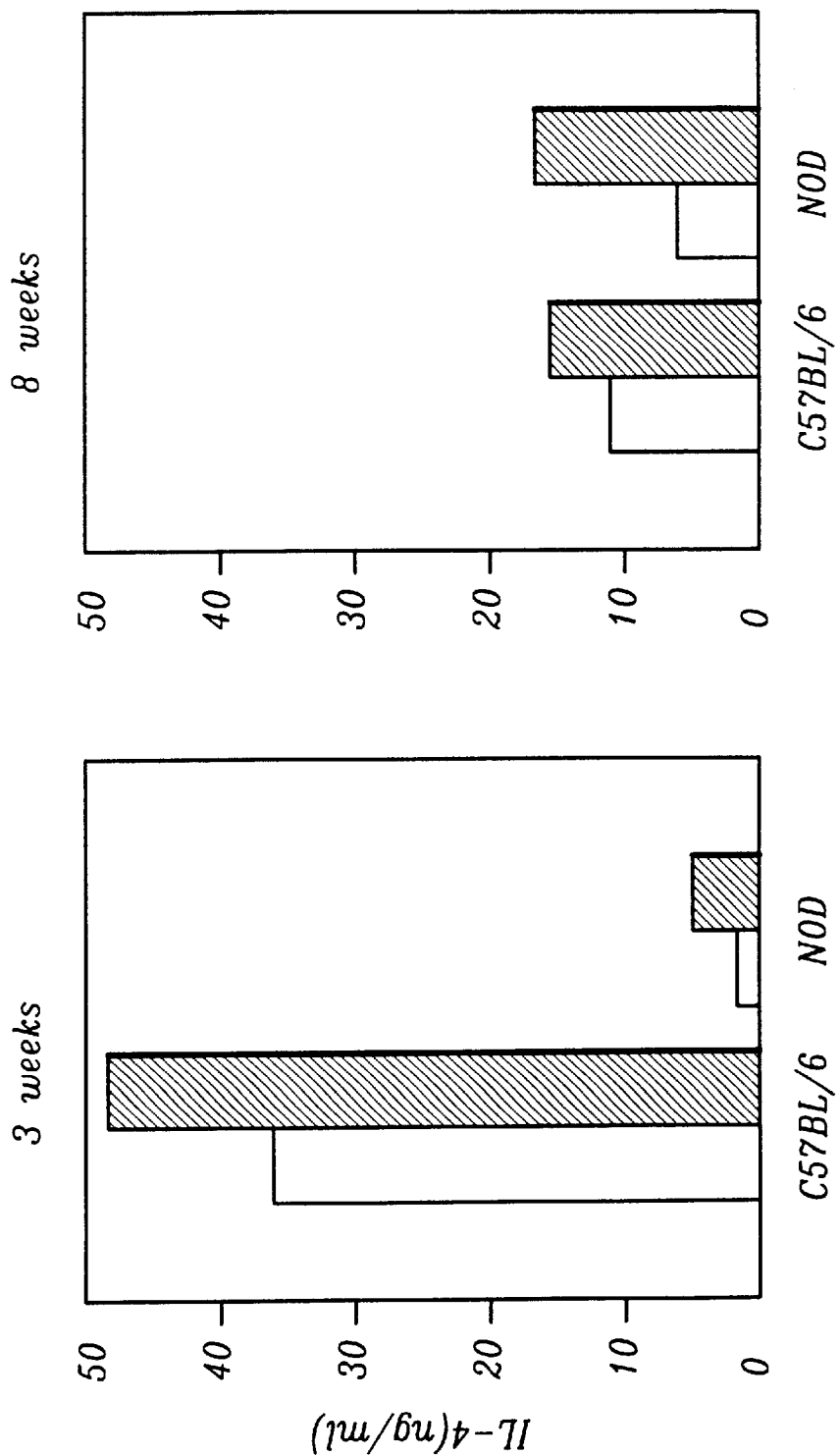

USE OF IL-7 FOR TREATING AUTOIMMUNE DISEASES AND INSULIN-DEPENDENT DIABETES MELLITUS IN PARTICULAR

The present invention relates to a novel use of interleukin-7 (IL-7) for treating autoimmune diseases, in particular insulin-dependent diabetes mellitus.

Type 1 diabetes or insulin-dependent diabetes mellitus (IDDM) is nowadays considered to be an autoimmune disease (Endocr. Rev. 1994, 15 (4), 516–542), characterised by the presence of anti-beta cell antibodies and by its sensitivity to immunosuppressive therapy. In both man and in the nonobese diabetic (NOD) mouse, IDDM results from a predominantly cellular type immune response, the humoral response being characterised by secretion of anti-membrane antibodies and secretary beta cell anti-products (N. Engl. J. Med. 1981, 304, 1454–1465, N. Engl. J. Med., 1992, 327, 302). The cellular type immune response is characterised by histological lesions or insulitis caused by infiltration of macrophage and B and T lymphocyte type inflammatory and immune cells into the islets of Langerhans of the pancreas (Diabetologia, 1989, 32, 282–289; Insulitis and type 1 diabetes, Academic Press Tokyo, 1986, 35–50).

The NOD mouse is a spontaneous model of autoimmune diabetes or type 1 diabetes. Converging arguments indicate that the onset of the disease is under the control of $CD4^+$ immunoregulatory T cells. It is accelerated by a thymectomy carried out at 3 weeks of age (Eur. J. Immuno. 1989, 19, 889–895) and can be prevented, in a transfer system, by co-injection of thymocytes or $CD4^+$ splenic cells from young not yet diabetic NOD mice (J. Exp. Med., 1989, 169, 1669–1680).

It has been indirectly suggested and demonstrated that, because of their ability to produce interleukin-4 (IL-4), T helper 2 (Th2) lymphocyte cells are the immunoregulatory $CD4^+$ cells in question (Autoimmunity, 1993, 15, 113–122). It has been demonstrated that administration of IL-4 (J. Exp. Med. 1993, 178 (1), 87–99) or anti-$\gamma$-interferon ($\gamma$-IFN) monoclonal antibodies prevent the onset of diabetes and administration of interleukin-12 (IL-12), the T helper 1 (Th1) lymphocyte inducer, accelerates the onset of diabetes (J. Exp. Med., 1995, 181 (2), 817–821).

However, a further study has shown that while diabetologically Th2-like cells discovered infiltrated into the islets do not cause the disease to appear, they do not afford significant protection (Science, 1995, 268 (5214), 1185–1188). Thus while it has been indirectly suggested and shown that the onset of diabetes in the NOD mouse is under the control of Th2 cells, no explanation has been given or suggested regarding the character of the anomaly present in the NOD mouse of the physiological process which occurs which is the origin of the emergence of an anti-Langerhans islets autoimmunity at the origin of diabetes in such animals. It has also recently been suggested that Th2 cell differentiation could be controlled by a T cell sub-type characterised by the TCR-$\alpha\beta$, $CD4^-CD8^-$ (double negative, DN) or $CD4^+CD8^-$ (simple positive) phenotype, carrying a mature phenotype (non-expression of heat stable antigen, HSA), selectively expressing the activation marker CD44. This sub-population, which is also characterised in other strains by the NK1.1 marker, has the ability to produce a large quantity of IL-4 after stimulation with an anti-TCR-$\alpha\beta$ polyclonal antibody (TCR-$\alpha\beta$: $\alpha\beta$ receptor of T cells) (J. Immunol. 1995, 155 (10), 4544–4550).

It has also been shown that this sub-type can be restricted by class I molecules of the major histocompatibility complex (MHC) and preferably uses the V$\beta$8 gene for the T receptor (J. Exp. Med., 1993, 178, 901–908), a sub-type proliferation of which is specifically induced by interleukin-7 (J. Exp. Med., 1994, 180 (2), 653–661).

Mammalian interleukin-7 proteins (cytokine IL-7s), in particular in man and in the mouse, the corresponding DNA, expression vectors coding for the IL-7s, and processes for their production, including recombinant systems, have been described (U.S. Pat. No. 4,965,195).

Mammalian interleukin-7 proteins will hereinafter be designated "IL-7". IL-7 is a lymphopoietic growth factor which can stimulate the development and proliferation of bone marrow cells (WO 89/03884). Stimulation of platelet production (WO 90/09194) by induction and proliferation of megacaryocytes was one of the first applications of IL-7. Other IL-7 applications have also been described such as cancer treatment or a treatment of a viral infection by immunotherapy from modified cells producing IL-7, either by direct injection of modified cells in vivo, or by a prior in vitro treatment phase before injection (WO 92/01459). The use of IL-7 for proliferating specific anti-HIV human T lymphocytes as a potential AIDS therapy (J. of Leucocyte Biology, 1995, 58 (6), 623–633), for treating malignant melanoma in dermatology (Hautarzt, 1995, 46 (10), 676–682), and as a potentialiser for a vaccine to prevent infection (microbial and viral) and tumours (WO 94/22473) have also been described. The use of an anti-IL-7 antibody for studying and researching physiological and pathological processes, in particular regarding differentiation and proliferation of lymphocytes (WO 94/28160), has also been described. Other applications combining the use of IL-7 with other cytokines have been described, such as the combination with IL-4 for in vitro induction of pre-B cell differentiation (WO 94/04658) or with IL-3 to treat leucopenia (WO 92/04465) and to prevent bone marrow disorders after cancer therapy or bone marrow grafts (WO 93/03061).

The authors of the present invention have shown here, on the basis of a phenotype study using flow cytometry using HSA, CD4, CD8, CD44 and V$\beta$8 markers, that a sub-population of thymocytes with phenotype $CD44^+TCR$-$\alpha\beta$ $HSA^-$ and preferably using the V$\beta$8 gene of the T receptor is numerically reduced in 3-week old NOD mice (both for the $CD4^-$-$CD8^-$DN (double negative $CD4^-CD8^-$) and $CD4^+$ (simple positive) populations and in 8-week old mice (for the DN population). It has also been discovered that at both ages this sub-population produces little or no IL-4. Finally, the authors of the present invention have shown that this double numerical and functional anomaly is corrected by IL-7 in vitro and in vivo, the growth factor for this cellular sub-population, and that IL-7 can protect mammals from diabetes, in particular insulin-dependent diabetes mellitus, this property also possibly extending to all autoimmune diseases, generated by a failure in the production of IL-4 by Th2 cells, in particular by the cellular sub-population described above, and generally to all autoimmune diseases, in particular those generated by a failure in immunoregulation by $CD4^+$ cells.

Thus in a first aspect, the present invention provides for the use of IL-7 or T lymphocytes incubated in the presence of IL-7 or modified lymphocytes producing IL-7 for the preparation of drugs or pharmaceutical compositions for treating autoimmune diseases, in particular autoimmune diseases generated by a failure in immunoregulation by $CD4^+$ T cells.

Preferably, the autoimmune diseases are autoimmune diseases generated by a failure in the production of IL-4 by Th2 cells.

Particularly preferably, the autoimmune diseases are autoimmune diseases generated by a failure in the production of IL-4 connected with a quantitative and functional deficiency of a T cell sub-type with phenotype HSA$^-$, CD4$^-$CD8$^-$ or CD4$^+$CD8$^-$, CD44$^+$, TCR-$\alpha\beta^+$, V$\beta$8$^+$, NK1.1$^+$.

In addition to insulin-dependent diabetes mellitus, other autoimmune diseases, autoimmune encephalo-myelitis, autoimmune rheumatoid arthritis, polyarthritis, autoimmune type 2 hepatitis, autoimmune gastritis, autoimmune sclerosis, sialadenitis, adrenalitis, oophoritis, glomerulonephritis, and autoimmune thyroiditis, can preferably be treated by said drugs or compositions, as can any autoimmune type pathogenic mechanism in a therapy associated with treatment of AIDS.

The autoimmune disease is preferably insulin-dependent diabetes mellitus.

Advantageously, the T lymphocytes previously incubated in the presence. of IL-7, used in the present invention, are autological or syngeneic cells from cells of the patients for whom the compositions comprising them are intended.

The invention also encompasses pharmaceutical compositions offering a novel approach for treating autoimmune diseases generated by a failure in immunoregulation by CD4$^+$ T cells.

In particular, the invention encompasses pharmaceutical compositions offering a novel approach for treating autoimmune diseases generated by a failure in the production of IL-4 by Th2 cells, particularly autoimmune diseases generated by a failure in IL-4 production connected with a quantitative and functional deficiency of a T cell sub-type with phenotype HSA$^-$, CD4$^-$CD8$^-$ or CD4$^+$CD8$^-$, CD44$^+$, TCR-$\alpha\beta^+$, V$\beta$8$^+$, NK1.1$^+$, in particular insulin-dependent diabetes mellitus.

Such compositions comprise IL-7 as the active principle, preferably in its soluble form, and/or autologous or syngeneic T lymphocytes from cells of a patient for whom the pharmaceutical composition is intended, said T lymphocytes having previously been incubated in the presence of IL-7. They can also be in the form of combinations with other active principles, for example other immunomodulating agents.

These different compositions can be administered in a number of different ways, as the skilled person will be able to determine, depending on the type of composition concerned.

Compositions comprising IL-7 as the active principle can be administered systemically, for example, preferably intravenously, intramuscularly, intradermally or orally.

Compositions comprising T lymphocytes as the active principle are preferably administered intravenously or intraperitoneally.

Preferred modes of administration, also dosages and optimum galenical forms, can be determined using the criteria which are generally considered in establishing a therapeutic treatment which is tailored to a patient, for example age or body weight of the patient, the seriousness of their general condition, tolerance to treatment and any known side effects.

The present invention also relates to a process for the production of a drug or pharmaceutical composition for treating autoimmune diseases, in particular autoimmune diseases generated by a failure in immunoregulation by CD4$^+$ T cells, characterised in that IL-7 and/or autologous or syngeneic T lymphocytes from cells of the patient for whom the composition is intended are mixed, said T lymphocytes having previously been incubated in the presence of IL-7 with a pharmaceutically acceptable vehicle or diluent, optionally combined with other active principles.

In particular, the invention concerns a process for the production of a drug or pharmaceutical composition for treating autoimmune diseases generated by a failure in IL-4 production by Th2 cells, in particular autoimmune diseases generated by a failure in IL-4 production connected with a quantitative and functional deficiency of a T cell sub-type with phenotype HSA$^-$, CD4$^-$CD8$^-$ or CD4$^+$CD8$^-$, CD44$^+$, TCR-$\alpha\beta^+$, V$\beta$8$^+$, NK1.1$^+$, in particular insulin-dependent diabetes mellitus.

The present invention concerns a therapeutic treatment method characterised in that a therapeutically effective dose of IL-7 or T lymphocytes which have previously been incubated in the presence of IL-7 is administered to a patient with an autoimmune disease, in particular an autoimmune disease generated by a failure in immunoregulation by CD4$^+$ cells.

Advantageously, the method of the invention is applicable to treating insulin-dependent diabetes mellitus.

Figure 2:
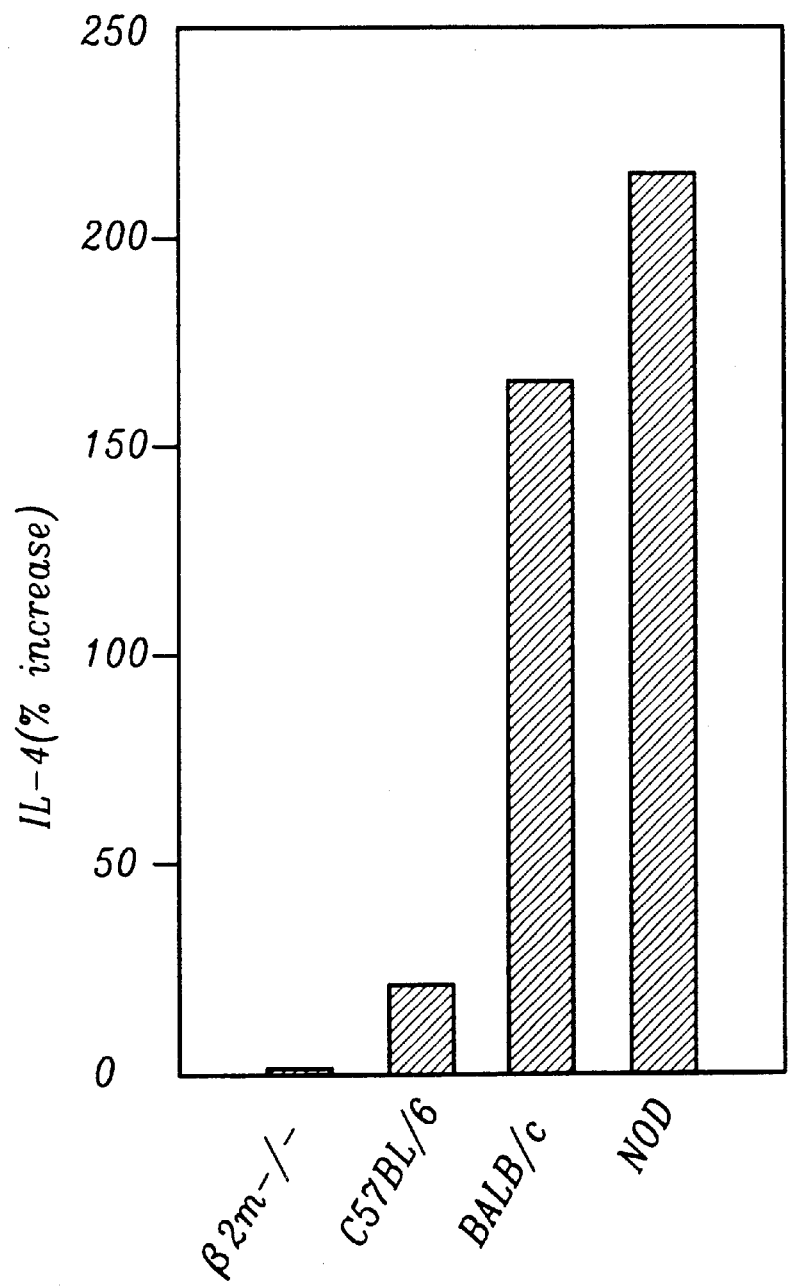

The present invention is illustrated by the accompanying FIGS. 1 and 2.

FIG. 1 shows the in vitro correcting effect of IL-7 on IL-4 production by mature HSA$^-$CD8$^-$ thymocyte cells in the young (FIG. 1*a*) and in the adult (FIG. 1*b*) NOD and C57BL/6 mouse.

In the experiment shown, freshly harvested HSA$^-$CD8$^-$ thymocytes from young (3 weeks old) or adult (8 weeks old) NOD or C57BL/6 mice were cultivated to 1.0×10$^5$ cells/well with an anti-TCR-$\alpha\beta$ monoclonal antibody in the presence (hatched column) or absence (open column) of 1000 U/ml of IL-7. The supernatant was recovered after 48 hours of incubation and measured for IL-4 using ELISA (average of 3 or 4 independent experiments).

Other features and advantages of the invention are apparent from the remaining description including the Examples and Tables summarising the results of the experiments.

FIG. 2 shows the effect of treating mice with IL-7 on the primary IL-4 production by splenocytes.

In the experiment shown, mice of different strains aged from 8 to 12 weeks received daily sub-cutaneous injections of 2 µg of IL-7 or bovine serum albumin (excipient) over 7 consecutive days. On the eight day, the mice were treated with anti-CD3 antibody then the cultivated splenocytes (5×10$^6$ cells per well) and IL-4 production was measured using the CT.4S test. The percentage increase in IL-4 production was calculated as follows: ((quantity of IL-4 produced after treatment with IL-7)/(quantity of IL-4 produced after treatment with excipient)−1)×100. The results are those of a typical experiment. The production of IL-4 (U/ml) by mouse splenocytes treated with excipient was respectively 94.3; 53.5; 11.0; and 11.4 for BALB/c, C57BL/6, NOD and C57BL/6$\beta$2m$^{-/-}$.

EXAMPLE 1

Study of the Ontogeny of CD44$^+$TCR-$\alpha\beta^+$ Thymocytes in the NOD Mouse Compared with the Non-diabetic C57BL/6 mouse Female NOD and C57BL/6 mice were kept under non-pathogenic specific environmental conditions. All of the NOD mice were verified as manifesting no evident sign of diabetes (no glycosuria or hyperglycemia). The thymus of about 5 to 15 exsanguine mice were carefully removed and mixed. The mature double negative (DN) and CD4$^+$ simple positive thymocytes were then enriched by incubation at 37° C. for 40 minutes with anti-CD8 antibodies (3–155; rat IgM described in J. Immunol. 1980, 125, 2665–2672), anti-HSA (J11d; rat IgM, Pharmigen) and anti-complement (rabbit complement, Low Tox, Cederlane, Ontario, Canada). Dead cells were then eliminated by density gradient centrifuging (J. Prep., Techgen, Les Ulis, France). Flow cytometry of the specific antibodies different to those used for cellular lysis showed that more than 95% of the recovered cells were of phenotype HSA$^-$CD8$^-$.

Marking was carried out as described in J. Exp. Med. 1994, 180, 653–661. The antibodies used were produced using commercially available hybridomas. Anti-TCR-$\alpha\beta$ (H57-597 clone, Pharmigen) or anti-V$\beta$8 antibodies (F23.1 clone described in J. Immunol. 143, 3994–4000), biotinylated or labelled with fluorescein (FITC), were used combined with anti-CD4 antibodies (RM 4.5 clone, Pharmigen) labelled with phycoerythrin (PE) and/or with anti-CD44 antibodies (IM 7.8 clone, Pharmigen) labelled with FITC.

For 3-colour labelling, after incubation in the presence of biotinylated antibodies, the cells were then incubated with the appropriate monoclonal antibodies labelled with FITC and PE and conjugated with streptavidin-Tricolor (SAv-Tri, Caltag).

The non-specific labelling reference was monitored in parallel. The apparatus used was a FACScan flow cytometer (Becton Dickinson, Mountain View, Calif.). The minimum sample was about $1\times10^4$ viable cells.

Cytokine production was measured from cells cultured in a medium as described in J. of Immunol., 1995, 155 (10), 4544–4550 and J. Exp. Med., 1994, 180, 653–661. About $10^5$ cells were deposited per well in round bottom cups of a 96 well microplaque (Nunc. Roskilde, Denmark), each test being repeated three times. The cups were covered with 10 $\mu$g/ml of anti-TCR-$\alpha\beta$ antibody (clone H57-597) and the cells were incubated for 48 hours in the presence or absence of 1000 U/ml of IL-7 (Sanofi, Toulouse, France) per 200 $\mu$l of final volume per well, the supernatant then being recovered and stored at $-70°$ C. before measuring the IL-4.

The IL-4 was measured using sandwich type ELISA, as described in J. of Immunol. 1995, 155 (10), 4544–4550.

The results obtained and shown in Table 1 below show that the appearance of the sub-population of thymocytes with phenotype TCR-$\alpha\beta^+$CD44$^+$, quantified among HSA$^-$CD8$^-$ T cells, was retarded in the NOD mouse compared with the C57BL/6 mouse with a very significant reduction observed at the age of 3 weeks.

TABLE 1

| STRAIN | AGE (WEEKS) | % of CD44$^-$TCR-$\alpha\beta^-$ in population of HSA$^-$CD8$^-$ thymocytes |
|---|---|---|
| C57BL/6 | 3 | *25.1 ± 0.8 |
|  | 8 | 27.9 ± 10.1 |
| NOD | 3 | 12.5 ± 0.3 |
|  | 8 | 25.3 ± 7.0 |

The results represent the average and the spread obtained for 4 to 5 independent experiments.
*p < 0.001 against 3-week old NOD mouse (Student's test).

Table 2 below shows the results obtained for double negative thymocyte populations (CD4$^-$CD8$^-$) and CD4$^+$ in 8 to 10-week old NOD and C57BL/6 mice. The level of the CD44$^+$ TCR-$\alpha\beta^+$ sub-population in the NOD mouse was still reduced at 8 weeks compared with the mouse with no autoimmune disease.

TABLE 2

| | *% of CD44$^-$TCR-$\alpha\beta^-$ in | |
|---|---|---|
| STRAIN | CD4$^+$ | CD4$^-$CD8$^-$ |
| NOD | 23 ± 8 | 34 ± 1 |
| C57BL/6 | 26 ± 10 | *59 ± 7 |

Average and spread obtained over 3 or 4 different experiments
*p < 0.001 against NOD strain (Student's test).

It was also verified that thymocyte cells characterised by the phenotype HSA$^-$CD8$^-$ CD44$^+$ exhibited the V$\beta$8 gene restriction mentioned above.

Similarly, it has been shown (FIG. 1) that HSA$^-$CD8$^-$ CD44$^+$ thymocyte cells in the control mouse would produce a large quantity of IL-4 when stimulated with an anti-TCR-$\alpha\beta$ monoclonal antibody while in the NOD mouse this production dropped dramatically at 3 and 8 weeks, even when taking the reduced number of HSA$^-$CD8$^-$CD44$^+$ cells into account (Table 1).

EXAMPLE 2

In vitro Correction by IL-7 of the Functional Deficit in the Thymocyte Sub-population in the NOD Mouse While it has already been shown that IL-7 specifically induces proliferation of the sub-population of HSA$^-$CD8$^-$ CD44$^+$ DN thymocytes (J. Exp. Med., 1994, 180, 653–661), the results obtained shown in FIG. 1 show in particular that, surprisingly, IL-4 production, measured on thymocytes after 48 hours of incubation in the presence of IL-7 and an anti-TCR-$\alpha\beta$ antibody, became normal again in the adult NOD mouse (8 weeks old), compared with the C57BL/6 mouse at an equivalent age.

EXAMPLE 3

In vivo Experiments Showing the Protective Effect of IL-7 on the Onset of Diabetes in the NOD Mouse The two experiments described below show that lymphoid cells originating from the thymus gland of the 3-week old NOD mouse can protect against the onset of diabetes in a co-transfer model. More precisely, 50 million total thymocytes from 3-week old NOD mice simultaneously injected with 5 to 10 million splenic cells from 10-week old diabetic NOD mice with irradiated NOD receptors prevented the onset of diabetes normally observed when splenic cells alone are injected. Injecting less than 10 million thymocyte cells had no protective effect. However, when the thymocytes had previously been incubated in vitro in the presence of IL-7 for 60 hours at 37° C., one million thymocytes afforded protection in the co-transfer model described above.

Further, it is known that one injection of cyclophosphamide (200 mg/kg) could cause the onset of diabetes in 8-week old male NOD mice in a much shorter time period (10 to 20 days) than that of spontaneous onset of diabetes (2 to 4 months). In vivo treatment with IL-7 consisting of 2 injections of IL-7, administered the day before and the day after injecting cyclophosphamide, protected against the onset of diabetes induced by cyclophosphamide.

These two series of experiments indicate that IL-7 plays a protective role against the onset of diabetes in genetically predisposed mice.

3.1 Protection Against Diabetes by Thymocytes Incubated in the Presence of Interleukin-7 in a Co-transfer Model Thymocytes were prepared from the thymus of 3-week old female NOD mice. These thymocytes were incubated in vitro for 60 to 72 hours at 37° C. in an RPMI medium containing 10% of foetal calf serum with added IL-7 (500–1000 U/ml). Following this incubation, 4, 2 or 1 million of these thymocytes and 5 or 10 million splenic cells from NOD mice which had recently become diabetic were simultaneously injected into 10-week old male NOD mice irradiated with a dose of 700 rad. Onset of diabetes was monitored three times a week by looking for glycosuria and confirmed when glycosuria was observed by evidence of hyperglycemia.

The results shown in Table 3 below show that thymocytes incubated in the presence of IL-7 protect against diabetes in doses which are not protective when thymocytes are used which are not incubated in the presence of IL-7.

TABLE 3

Protective effect of total thymocytes treated with IL-7 in a model of diabetes induced by passive transfer of cells originating from diabetic mice

| Experiment | Transferred thymocytes | Number of animals | Number of diabetic mice as a function of number of weeks after transfer | | | |
|---|---|---|---|---|---|---|
| | | | 1 w.* | 4 w.* | 6 w.* | 8 w.* |
| No 1 | — | 6 | 0 | 4 | 5 | 5 |
| | untreated | 6 | 0 | 3 | 4 | 6 |
| | treated with IL-7 | 6 | 0 | 0 | 0 | 1 |
| No 2 | — | 5 | 0 | 0 | 4 | 4 |
| | treated with IL-7 | 8 | 0 | 0 | 0 | 0 |
| No 3 | — | 8 | 0 | 6 | 6 | NT |
| | treated with IL-7 | 6 | 0 | 0 | 0 | NT |

NT: not tested.
*w : week(s)

3.2 Protection Against Diabetes Induced by Infecting Cyclophosphamide, Using Injections of Interleukin-7

6 to 7-week old female NOD mice received one injection of 200 mg/kg of cyclophosphamide, framed on days −1 and +1 by an intravenous injection of 1 µg of IL-7. Onset of diabetes was detected by looking for glycosuria and hyperglycemia as described in Example 1.

The results shown in Table 4 indicate that treatment with IL-7 significantly prevented the onset of diabetes compared with mice which received cyclophosphamide with no IL-7.

TABLE 4

Protective effect of IL-7 in the cyclophosphamide induced diabetic model

| Treatment | Number of mice | Number of diabetic mice after 2 weeks following injection of cyclophosphamide |
|---|---|---|
| — | 10 | 8 |
| IL-7 | 10 | 2 |

These results show that NOD mice have a premature deficit of a sub-population of thymocytary HSA⁻CD8⁻TCR-αβ⁺ cells, expressing the marker CD44, with the Vβ8 restriction and having the ability to produce IL-4 (termed T NK1⁺ cells, recently identified in non-autoimmune strains). This numerical deficit is surprisingly associated with a functional deficit expressed as a large reduction in IL-4 production.

The results indicate that the anomaly of this deficit in NOD mice, affecting both the sub-populations of CD4⁻CD8⁻ (DN) and CD4⁺ (simple positive) thymocytes, is corrected in vitro by using IL-7.

Further, the in vivo experiments, whether by injecting cells which had previously been incubated in the presence of IL-7 or by direct injection of an effective quantity of IL-7 into the mouse, demonstrated that the use of IL-7 had a protective effect against the onset of an autoimmune disease, in particular diabetes.

EXAMPLE 4

In vivo Treatment with IL-7

In vivo treatment with IL-7 potentialises the production of IL-4 by splenic T cells (FIG. 2). This effect of IL-7 was obtained in all of the mouse strains tested (C57BL/6, BALB/c, NOD) and was a maximum in the autoimmune NOD mouse which had a deficit of peripheral IL-4 production (see legend of FIG. 2). The absence of an increase in IL-4 production in C57BL/6 mice without the β2-microglobulin gene and thus deficient in T NK1⁺ cells suggests that the action of the IL-7 is targeted to T NK1⁺ cells.

The sub-cutaneous IL-7 injection protocol comprised two doses of 2 µg per day for 4 to 7 consecutive days. Control mice were treated with an identical volume of excipient solution (bovine serum albumin). IL-4 production was raised after a single intravenous injection (1.33 µg) of an antibody directed specifically against the murine CD3 molecule (anti-CD3, clone 145-2C11, hamster IgG). The animals were sacrificed 90 minutes following injection of the anti-CD3 antibody; the spleens were immediately removed and splenic cells cultured for 90 minutes in the absence of any stimulation (Yoshimoto et al., J. Exp. Med., 179, 1285–1295). The RPMI medium, containing decomplemented foetal calf serum (10%), β-mercaptoethanol (0.05 mM) and antibiotics (penicillin, 100 Ul/ml and streptomycin, 100 µg/ml), was used for all of the cell culture experiments. The supernatants were removed and their IL-4 content determined using the CT.4S biological test, a line dependent on IL-4 (Hu-Li et al., J. Immunol., 142, 800–807). The IL-4 concentration was expressed as U/ml (one unit corresponded to approximately 1 pg) following a standard curve established with serial dilutions of recombinant murine IL-4. The sensitivity limit of the test was about 10 U/ml.

The absence of peripheral IL-4 production by T NK1+ cells in the NOD mouse could explain the deficit in the Th2 function which accompanies the emergence of diabetogenic Th1 type cells responsible for the autoimmune disease in this strain.

These results, which constitute the first demonstration of an in vivo pharmacological effect of IL-7 on the production of IL-4 by T NK1+ cells, sheds light on the protective role of IL-7 as regards the appearance of autoimmune diabetes. More generally, the experimental data enables IL-7 to be proposed for use as a therapeutic weapon for diverting the immune response in favour of a Th2 type profile.

What is claimed is:

1. A method for the treatment of insulin-dependent diabetes mellitus which comprises administering to a patient in need of such treatment a therapeutically effective amount of interleukin-7.

* * * * *